(12) United States Patent
Lemaire

(10) Patent No.: US 6,573,421 B1
(45) Date of Patent: Jun. 3, 2003

(54) ADHESIVE BANDAGE

(75) Inventor: Serge Lemaire, Saint-Clement-de-Riviere (FR)

(73) Assignee: Internova International Innovation Company B.V., Rotterdam (NL)

( * ) Notice: Subject to any disclaimer, the term of this patent is extended or adjusted under 35 U.S.C. 154(b) by 0 days.

(21) Appl. No.: 10/018,423

(22) PCT Filed: Jun. 13, 2000

(86) PCT No.: PCT/IB00/00797
§ 371 (c)(1),
(2), (4) Date: Dec. 13, 2001

(87) PCT Pub. No.: WO00/76440
PCT Pub. Date: Dec. 21, 2000

(30) Foreign Application Priority Data

Jun. 16, 1999 (FR) .............................. 99-07800

(51) Int. Cl.⁷ ............................... A61F 13/00
(52) U.S. Cl. ............... 602/57; 602/52; 602/41
(58) Field of Search ............... 602/41–43, 52, 602/54, 56, 57, 60, 78; 604/389–390; 206/440, 441; 24/304

(56) References Cited

U.S. PATENT DOCUMENTS

| | | | | |
|---|---|---|---|---|
| 4,264,008 A | * | 4/1981 | Kozlow |
| 4,265,234 A | * | 5/1981 | Schaar |
| 4,304,333 A | * | 12/1981 | Kozlow, Sr. |
| 4,884,563 A | * | 12/1989 | Sessions |
| 4,928,680 A | * | 5/1990 | Sandbank |
| 5,000,172 A | * | 3/1991 | Ward |
| 5,052,381 A | * | 10/1991 | Gilbert et al. |
| 5,074,293 A | * | 12/1991 | Lott et al. |
| 5,092,323 A | * | 3/1992 | Riedel et al. |
| 5,275,284 A | * | 1/1994 | Onotsky |
| 5,397,297 A | | 3/1995 | Hunter |

FOREIGN PATENT DOCUMENTS

| | | |
|---|---|---|
| EP | 0 308 122 A | 3/1989 |
| GB | 2 224 445 A | 5/1990 |
| WO | 97 28771 A | 8/1997 |

* cited by examiner

*Primary Examiner*—Nicholas D. Lucchesi
*Assistant Examiner*—Lalita M Hamilton
(74) *Attorney, Agent, or Firm*—Davis & Bujold, P.L.L.C.

(57) ABSTRACT

The invention concerns an adhesive bandage (10) comprising a support (11) with an adhesive surface (12), a sterile pad (13) arranged on the adhesive surface and a protective film covering the adhesive surface and the sterile pad, which is formed by a first (14) and a second (15) tearaway tab. The first tab (14) is folded back on itself along a folding line (16), outside the sterile pad zone, to define a first flap (17) applied on the adhesive surface from a first end of the support up to the folding line and covering entirely the sterile pad, and a second flap (18) forming a tearing lead for the first flap and extending over the first flap beyond the support first end. The second tab (15) comprises a third flap (19) applied on the adhesive surface from the second end of the support up to the folding line, and a fourth flap (20) forming a tearing lead for the third flap which extends over the first tab from the folding line beyond the support first end.

12 Claims, 3 Drawing Sheets

ADHESIVE BANDAGE

FIELD OF THE INVENTION

The present invention concerns an adhesive bandage, in particular, for application on an acutely affected area of the epidermis which is very sensitive to contamination by bacterial germs and must remain sterile and, notably, an area containing a site for the implanting of an arteriovenous fistula forming a vascular access to a patient on hemodialysis, the said adhesive bandage comprising a support having an adhesive side, a sterile pad positioned on the said adhesive side of the support and a protective film covering the adhesive side and the sterile pad, the said protective film being made up of a first and second detachable tab, the said first detachable tab being folded back on itself along a folding line, outside the sterile pad area, and comprising a first flap applied on the adhesive side of the support and which extends at least from a first extremity of the said support towards its interior until the said folding line so as to cover entirely the sterile pad, and a second flap consisting of a beginning which tears off from the said first flap and which extends over the said first flap from the said folding line in the direction of the said first extremity of the support, the said second detachable tab comprising a third flap applied on the adhesive side of the support and which extends, outside of the sterile pad area, at the least from a second extremity of the said support, opposite the said first extremity, towards the interior of the said support until the said folding line of the first detachable tab.

BACKGROUND OF THE INVENTION

An adhesive bandage of the type described above is presented by the American patent U.S. Pat. No. 5,397,297. Its second detachable tab, shorter than the first, also folds back on itself in the shape of a V. It consists of a fourth flap, which tears off and which extends over the third flap from the folding line beyond the second extremity of the support.

The sole aim of this patent is to present a particular packaging for a band age in an individual wrapping which facilitates the application of the bandage, without giving any guarantee for the sterility of this application. The two tearing flaps of the two tabs are sealed inside opposite extremities of the wrapping, forming two traction areas. This wrapping comprises, as well, on a longitudinal edge, a notch that is aligned with the folding line of the two tabs, as well as an area of prehension, facing the second tab and the bandage support.

To apply the bandage, the user must hold the wrapping in its prehension area then pull on the first traction area, connected to the tear-off flap of the first tab. The wrapping tears in two sections along the folding line of the tabs. The first tab, which entirely covers the pad, is pulled back first from the adhesive side of the support. The second tab stays in place on the support. From then on, there is a very high risk that the surrounding air or the user's fingers will contaminate, with bacterial germs, the pad and the large section of the support's adhesive side, which are uncovered. When this contaminated section is applied to the affected area of the skin, the germs it contains can cause serious infections.

Another adhesive bandage of a similar type is described in the English patent application published under the number GB-A-2 224 445. This bandage comprises a support provided with an adhesive surface which is protected by two detachable tabs. The first tab is folded back on itself in a V.

It defines a first flap, applied on a small section of the adhesive surface towards the interior of the support from a first extremity, and a second flap which tears off from the first tab extending towards the exterior of the support beyond its first extremity. The second tab is more or less flat. It defines a third flap, applied on a large section of the adhesive surface towards the interior of the support from its second extremity, and a fourth flap, tearing from the second tab, which covers the first tab and extends beyond the first extremity of the support.

This adhesive bandage does not comprise a sterile pad on the adhesive surface for application on the affected area of the epidermis. The sole object of this patent application is to propose an adhesive bandage which is easy to apply, without offering any guarantee for the sterility of this application. Moreover, the second tab, whose third flap covers the large section of the support's adhesive surface, must be pulled back first. Therefore, there is a very high risk of serious contamination, by the surrounding air and by the user's fingers, of a large section of the adhesive surface before its application to the affected area of the skin, which would, itself, become seriously infected.

It is known other adhesive bandages similar to those previously described, notably in the international patent application published under the number WO 97 28771 and the European patent application published under the number EP-A-0 308 122. These bandages have various disadvantages and, in particular, do not guarantee systematic sterile application and present high risks of contamination to the affected area of the epidermis.

Consequently, the previous adhesive bandages are unsuitable for application on an acutely affected area of the epidermis which is very sensitive to contamination by bacterial germs and must remain sterile and for which a risk, even minimal, of contamination is not admissible.

SUMMARY OF THE INVENTION

The present invention proposes to overcome this major disadvantage by providing an adhesive bandage which can be packaged under sterile conditions before use and which is provided with a protective film allowing the bandage to be manipulated without special precaution and for the adhesive side and the sterile pad of the support to be easily applied, even with one hand, to the patient's skin under systematically sterile conditions.

This aim is achieved by an adhesive bandage such as described in the preamble and characterised in that the said second detachable tab is designed to be lifted from the adhesive side of the support before the first detachable tab, in that the said second flap extends over the said first flap at least beyond the sterile pad area in the direction of the said first extremity of the support, and in that the said second detachable tab comprises a fourth flap with a beginning which tears off from the said third flap and which extends over the said first detachable tab from the said folding line at least beyond the sterile pad area in the direction of the said first extremity of the support.

The said fourth flap preferably has a length greater than that of the said first flap and extends beyond the said first extremity of the support.

The said second flap preferably has a length greater than that of the said first flap and extends beyond the said first extremity of the support.

In one advantageous embodiment, the said second flap has a length greater than that of the said fourth flap and extends beyond the said fourth flap.

BRIEF DESCRIPTION OF DRAWINGS

This invention and its advantages will be more apparent from the description of a preferred embodiment of the invention and with reference to the annexed drawings in which.

DESCRIPTION OF THE PREFERRED EMBODIMENT

Figure 1:
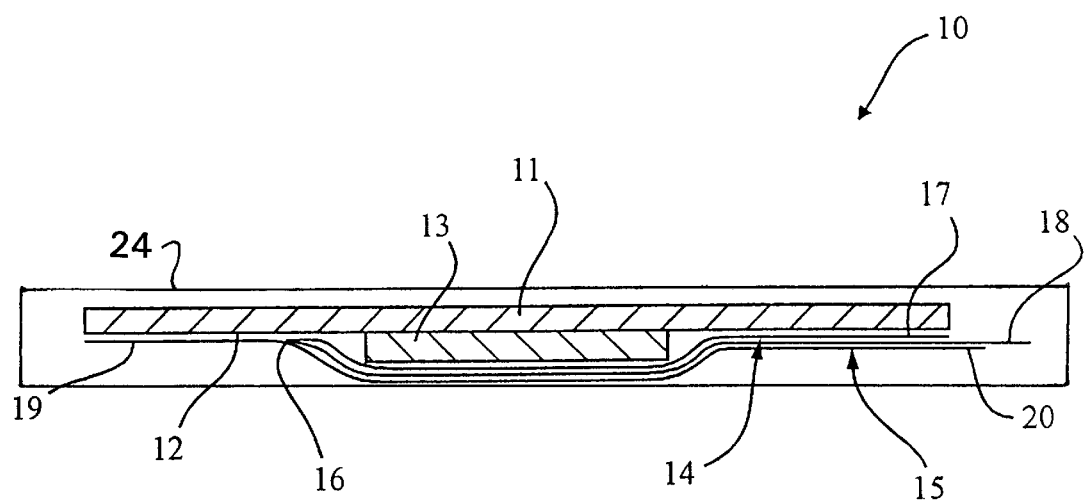
FIG. 1 is a lateral sectional view of the adhesive bandage of the invention.

The adhesive bandage 10 comprises a support 11, of, for example, a substantially rectangular shape, provided with an adhesive side 12 and a sterile pad 13 positioned on this adhesive side 12, for example in its central zone. The bandage 10 also comprises a protective film, subject of the invention, which is made up of two detachable tabs 14 and 15.

The first tab 14 is folded back on itself along a folding line 16 substantially perpendicular to the longitudinal axis of the support 11 and outside the area of the sterile pad 13. It consists of a first flap 17 which is applied on the adhesive side 12 of the support 11. This flap 17 extends from a first extremity of the support 11 towards its interior until the folding line 16, in such a way as to cover completely the sterile pad 13. The first tab 14 also has a second flap 18 consisting of a beginning which tears off from the first flap 17. This second flap 18 extends over the first flap 17, beyond the area of the sterile pad 13, from the folding line 16 in the direction of the first extremity of the support 11. It has a length greater than that of the first flap 17 and extends beyond this first extremity of the support 11.

The second detachable tab 15 is substantially flat and has no folding zone. It comprises a third flap 19 which is applied on the adhesive side 12 of the support 11. This flap 19 extends, outside of the area of the sterile pad 13, from a second extremity of the support 11, opposite its first extremity, towards the interior of the support 11 until the folding line 16 of the first tab 14. The second tab 15 comprises a fourth flap 20 consisting of a beginning which tears off from the third flap 19. This fourth flap 20 extends over the first tab 14, beyond the area of the sterile pad 13, from the folding line 16, in the direction of the first extremity of the support 11. It has a length greater than that of the first flap 17 and extends beyond the first extremity of the support 11. This fourth flap 20 of the second tab 15 is favourably shorter than the second flap 18 of the first tab 14 so that this second flap 18 extends beyond the fourth flap 20.

Figure 2:
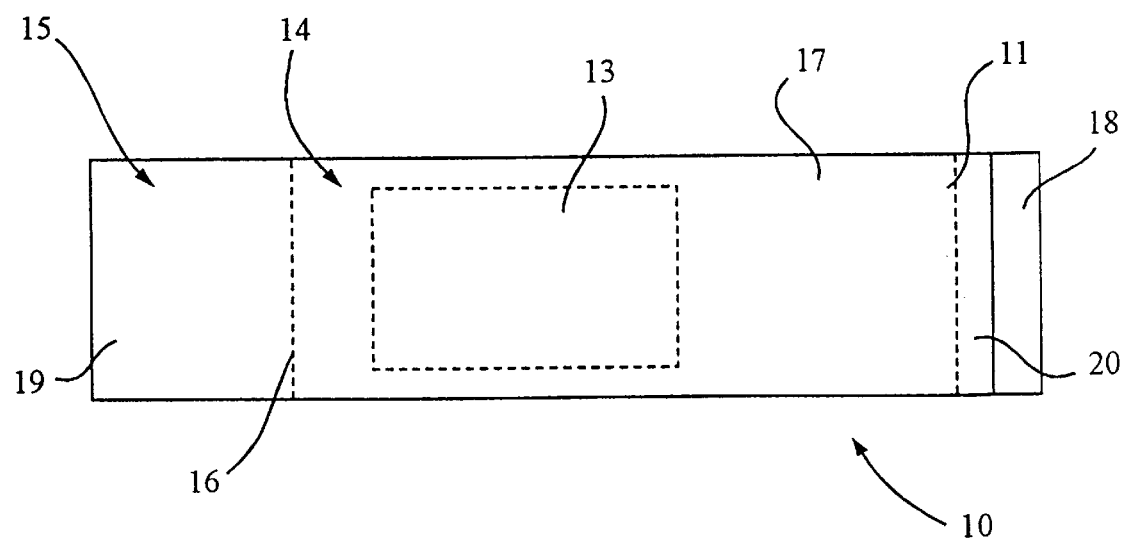
FIG. 2 is a view of the underside of the adhesive bandage in FIG. 1.

Before use, the adhesive bandage 10 is packaged under sterile conditions in a closed, individual package or wrapping 24 (only diagrammatically shown in FIG. 1). This wrapping 24 forms an absolute barrier against germs and can also be impervious to liquids. To facilitate its opening, it can have a pre-fold or a notch, so that the user can easily open it, for example by tearing, without risk of damage to the bandage contained in it. The bandage 10 is placed in this wrapping 24 in the initial configuration described previously and illustrated by FIGS. 1 and 2, in which flaps 17, 18 of the first tab 14 and the fourth flap 20 of the second tab 15 are superposed, over the area of the sterile pad 13.

We shall now describe the application of the adhesive bandage 10 with reference to FIGS. 3a to 3g which represent the different sequences of the application.

Firstly, the user tears the wrapping and takes in one hand, the adhesive bandage 10 contained in the wrapping. The second tab 15 covers the adhesive side 12 over the small section of the support 11, defined between the second extremity of the support 11 and the folding line 16, as does the first tab 14 over the large section of the support 11, defined between the folding line 16 and the first extremity of the support 11, which contains the sterile pad 13. The second tab 15 therefore effectively protects these two sections from any contamination by the surrounding air and by the user's fingers. Only the inferior side or exterior side of the second tab 15 can be contaminated but this does not constitute any risk of subsequent contamination for the patient during application of the adhesive bandage 10, as will be explained below. The user can therefore manipulate the bandage without particular precaution.

Figure 3A:
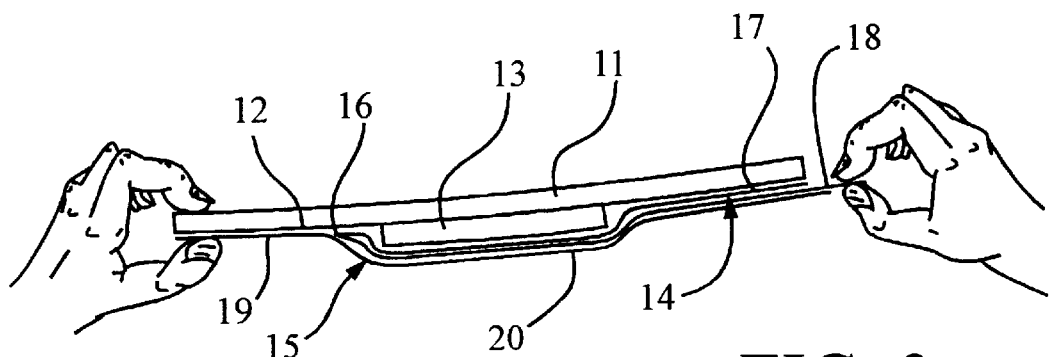
FIGS. 3a to 3g represent the sequences for application of the adhesive bandage in FIGS. 1 and 2.
Figure 3B:
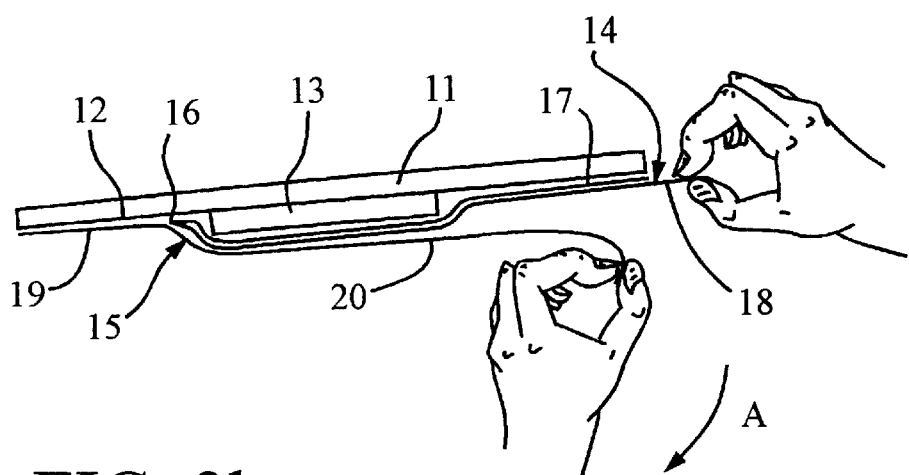

We now refer to FIG. 3a. Firstly, the user grips in one hand the second extremity of the support 11 with the third flap 19 of the second tab 15, then, with the other hand, takes the second flap 18 which tears off from the first tab 14, what is relatively easy as this flap 18 extends beyond the first flap 17 and beyond the fourth flap 20. Next, referring to FIG. 3b, he takes with his first hand the fourth flap 20 tearing from the second tab 15, which extends beyond the first extremity of the support 11. At this moment, the second flap 18, from the side corresponding to the fourth flap 20, has never been in contact with the user's fingers and is therefore still sterile on the large section of the support 11, to the right of the folding line 16 and containing the sterile pad 13. The user then pulls the fourth flap 20 towards the second extremity of the support 11, in the direction indicated by the arrow A, to unstick the third flap 19 from the small section of the adhesive side 12 of the support 11, to the left of the folding line 16, see FIG. 3c.

This section of the adhesive side 12, which is still sterile, may be applied on the skin 21 of the patient at the appropriate place, that is, next to the affected area 22 of the epidermis which needs to be covered at the end of the application by the sterile pad 13, as the third flap 19 is being detached from the adhesive 12 and it is uncovered. This limits its exposure to the surrounding air.

Figure 3C:
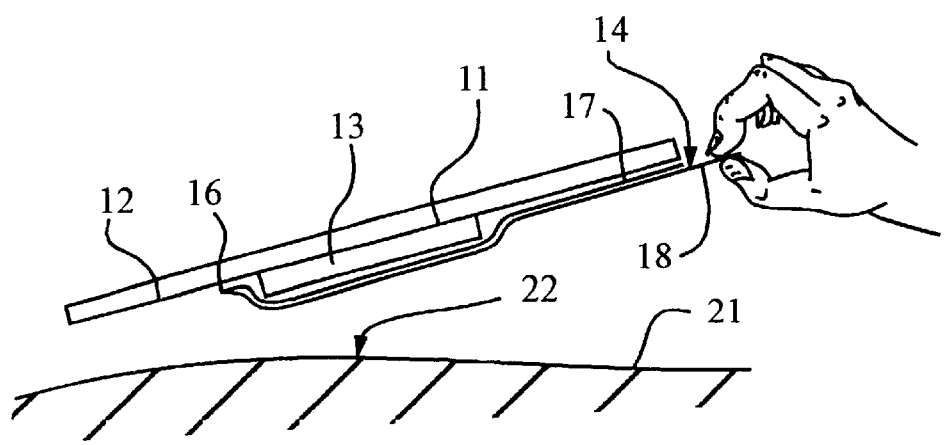

It should be noted that the third flap 19 can be detached entirely from the small section of the adhesive side 12, as represented in FIG. 3c, before this is stuck to the skin 21 of the patient, which allows the application of the adhesive bandage 10 to be terminated with one hand only. In this case, the small uncovered section of the adhesive side 12 is only lightly and for a very short time in contact with the surrounding air and remains almost sterile. However, a minimum contamination of the adhesive side 12 outside of the sterile pad area 13 does not pose any risk of contamination to the affected area 22 adjacent to the epidermis, which will be covered at the end of the application by the sterile pad 13.

Figure 3D:
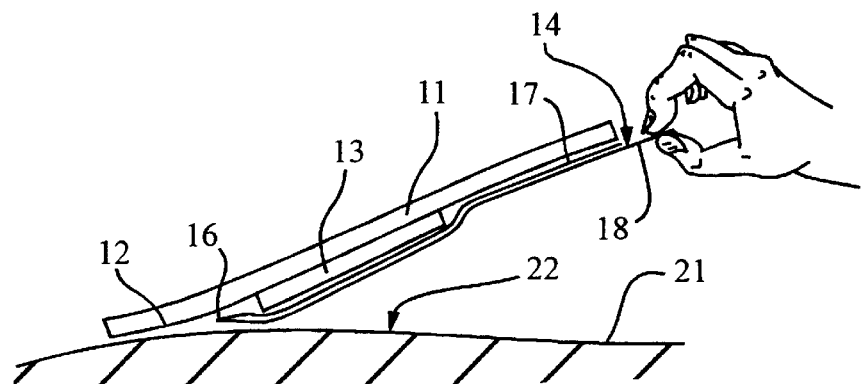

Referring now to FIG. 3d, the small section of the adhesive side 12, to the left of the folding line 16, is from now on stuck to the skin 21 of the patient. The inferior side of the second flap 18, which up till now was protected by the fourth flap 20 of the second tab 15, is now facing the skin 21 of the patient and the affected area 22 of the epidermis. However, this side of the second flap 18 has never been in contact with the user's fingers, in particular in the sterile pad 13 area, and can therefore touch the affected area 22 of the epidermis without any risk of contamination. It should also be emphasized that the large section of the adhesive side 12 of the support 11, to the right of the folding line 16, and the sterile pad 13 are still totally covered by the first flap 17 of the first detachable tab 14 and are still perfectly sterile.

Figure 3E:
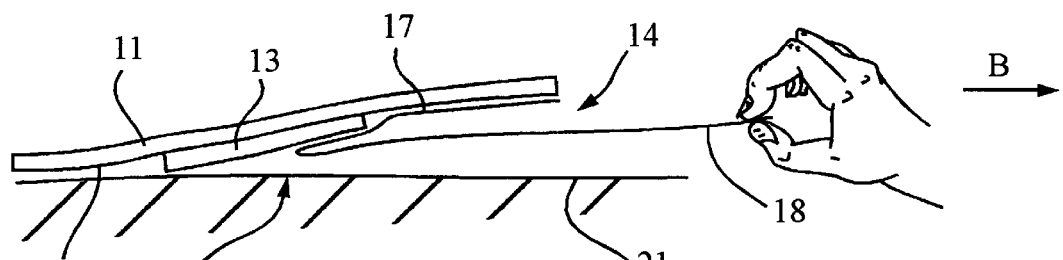
Figure 3F:
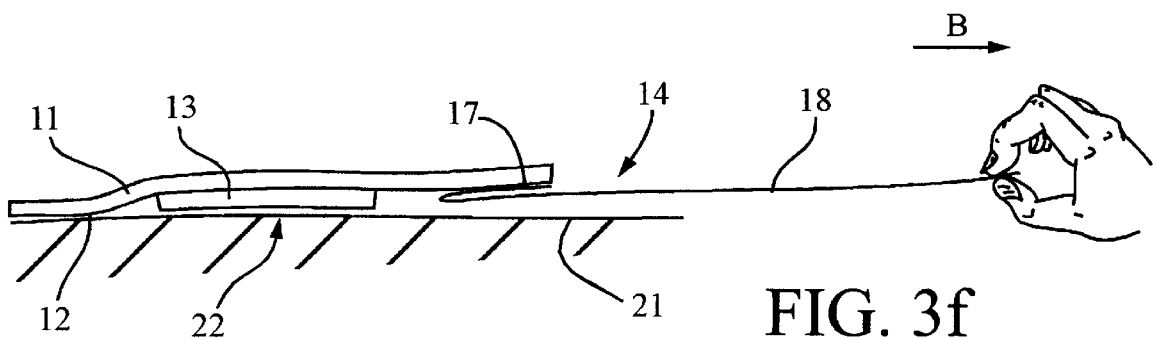
Figure 3G:
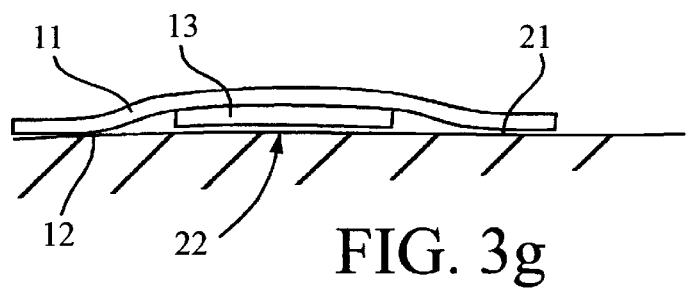

Finally, referring to FIGS. 3e to 3g, the user pulls the second flap 18, tearing from the first detachable tab 14 towards the exterior of the support 11, in the direction indicated by the arrow B, to unstick the first flap 17 of the large section of the adhesive side 12 of the support 11, to the right of the folding line 16. The adhesive side 12 of the support 11 is uncovered and sterile and, as it is being uncovered, sticks to the skin 21 of the patient. The sterile pad 13 has therefore been applied under perfectly sterile conditions on the affected area 22 of the epidermis.

The protective film of the adhesive bandage 10 of the invention has a number of advantages. The second detachable tab 15 of the protective film effectively protects the bandage 10 when it is removed from its wrapping and allows it to be manipulated without special precaution and without any risk of subsequent contamination to the patient. The flaps 18, 20 tearing from the detachable tabs 14, 15 allow easy application of the bandage 10 to the skin, even with only one hand and under systematically sterile conditions. This is because the sides of the flaps 17 to 20, which could be in contact with the affected area 22 of the epidermis during application of the support 11, have never been in contact with the user's fingers. They are therefore still sterile and there is no risk of contamination. Furthermore, the adhesive side 12 and the sterile pad 13 of the support 11 are applied rapidly to the skin 21 of the patient, as soon as they are uncovered, which also removes the risk of contamination by the surrounding air.

The adhesive bandage 10 of the present invention is particularly well adapted to applications requiring optimum sterile conditions and for which the slightest risk of contamination of the affected area of the epidermis can have serious, even fatal, consequences, and must be prevented. Examples of critical applications are those performed in an operating theatre, notably for the covering of laparotomy or thoracotomy wounds, burns or similar.

A particularly critical application of an adhesive bandage would be in the area of dialysis. A patient suffering chronic renal problems has to follow regularly, sometimes daily, a treatment of blood dialysis in a hospital environment or at home. At each session, an artery and a vein of the patient's circulatory system must be connected to a dialysis machine to purify the patient's blood. So as to facilitate this treatment and relieve the patient, the patient has an implanted arteriovenous fistula permanently during surgical procedure. This is implanted under the epidermis of the upper-arm and is connected at each session to the dialysis machine. This gives permanent vascular access to the patient and must always be covered with a sterile adhesive bandage for two reasons. The bandage serves, partly, to maintain the fistula's vascular access at the patient's upper-arm as, should this be lost, surgery would then be needed to recreate it. Principally, however, it serves to protect it from contamination by bacterial germs so as to avoid a latent septicaemia in the patient, who is already ill and fragile. To guarantee protection and lasting sterility, the adhesive bandage applied to the arm must be replaced regularly, at least after each session, and often by the patient himself. This would necessarily be with one hand. Consequently, the adhesive bandage used must systematically allow for perfectly sterile application, even with one hand, without the risk of any subsequent contamination. The adhesive bandage 10 of the invention responds to all these stringent criteria of application.

Of course, the adhesive bandage 10 of the invention suits other, less serious, applications as far as sterility is concerned. The adhesive bandage can be the occlusive type, the support 11 and the sterile pad 13 then being gaspermeable but impervious to liquids and to bacteria. The support 11 can be transparent, made, for example, from polyurethane, so that the surface of the covered skin 21 is visible. The adhesive side 12 can equally be hypoallergenic. The adhesive bandage 10 may be hydroactive, the sterile pad 13 then containing water with additional agents allowing decomposition, for example to promote the healing of a wound. The adhesive bandage 10 can have any dimensions, be small or large, and be any shape, rectangular, oval or circular, for example.

The adhesive bandage can be produced simply and economically on conventional machines. One detachable tab 14 is folded back on itself, while the other detachable tab 15 does not have a folding section. As the second tab 15 covers the support over its entire length, the relative tolerance of its position from the folding line 16 of the first tab 14 on the adhesive side 12 can be large. It needs only be situated outside the area of the sterile pad 13. The folding of the detachable tab 14 is always done outside the area of the sterile pad 13, the latter conserving all its effectiveness. Moreover, the adhesive bandage 10 can be packaged under sterile conditions in any sort of individualized wrapping, as the second detachable tab 15 protects the bandage 10 effectively when it is removed from its wrapping.

The present invention is not limited to the types of implementation already described and illustrated but extends to any modification and variant evident for those in the profession. For example, the support 11 may be covered on its superior non-adhesive side, with a layer of detachable reinforcement which is removed after application of the support on the skin. This means, firstly, that the support does not become creased during application if it is too soft, but, also, that contact with the fingers on the superior side of the support is avoided, and so improves the sterility of the application.

To guarantee the sterility of the application of the pad 13 on the affected area of the epidermis, the only essential is that the fourth flap 20 of the second detachable tab 15 extends over the second flap 18 of the first detachable tab 14 and that the two tearing flaps 18, 20 extend from the folding line 16, at least beyond the area of the sterile pad 13 in the direction of the first extremity of the support 11. The fact that these two flaps 18, 20 are longer than the first flap 17 and extend beyond the first extremity of the support 11 allows, on one hand, easier manipulation of the bandage 10 during its application, and on the other hand, to guarantee, beyond the sterility of the application of pad 13 on the affected area of the epidermis, the sterility of the application of the adhesive side 12 of the support 11 on the patient's skin around the affected area 22 covered by the sterile pad 13. Moreover, the fourth flap 20 of the second detachable tab 15 may have a length greater than that of the second flap 18 of the first detachable tab 14 and extend beyond the first extremity of the support 11 and the second flap 18.

What is claimed is:

1. An adhesive bandage for application to an acutely affected area of epidermis which is sensitive to contamination by bacterial germs and must remain sterile, the adhesive bandage comprising:

a support having an adhesive side with a sterile pad situated on the adhesive side of the support, a protective film covering and the sterile pad and the adhesive side, the protective film having first and second detachable tabs, the first detachable tab comprising a first flap and a second flap separated from one another by a folding line, the first flap being applied to the adhesive side of the support and extending from a first extremity of the support toward a second extremity of the support so as to cover a portion of the adhesive side adjacent the first extremity and entirely cover the sterile pad with the folding line of the first detachable tab being located adjacent the sterile pad, and the second flap extends from the fold line, in a direction back toward the first extremity of the support, so as to fold back over the first flap; and the second detachable tab comprising a third flap applied to the adhesive side of the support at least adjacent the second extremity, and a remote end of the second detachable tab extending toward the first extremity;

wherein the second flap (18) extends, in the direction of the first extremity of the support (11), over the first flap (17) at least beyond an area of the sterile pad (13) so as to cover completely the sterile pad (13), the second detachable tab (15) comprises a fourth flap (20), formed integral with the third flap (19), which extends, commencing at the folding line (16), in the direction of the first extremity of the support (11) over the first detachable tab (14) at least beyond the sterile pad (13) so as to cover completely the sterile pad (13), and the second detachable tab (15) is arranged to be removed from the adhesive side (12) of the support (11) before the first detachable tab (14).

2. The adhesive bandage according to claim 1, wherein the fourth flap (20) has a length greater than a length of the first flap (17) and extends beyond the first extremity of the support (11).

3. The adhesive bandage according to claim 2, wherein the second flap (18) has a length greater than a length of the fourth flap (20) and extends beyond the fourth flap (20).

4. The adhesive bandage according to claim 1, wherein the second flap (18) has a length greater than a length of the first flap (17) and extends beyond the first extremity of the support (11).

5. The adhesive bandage according to claim 1, wherein the fourth flap (20) has a length greater than a length of the first flap (17) and extends beyond the first extremity of the support (11); and the second flap (18) has a length greater than a length of the first flap (17) and greater than a length of the fourth flap (20), and the second flap (18) extends beyond the first extremity of the support (11) and beyond the fourth flap (20).

6. The adhesive bandage according to claim 1, wherein the acutely affected area of the epidermis is a site for implementation of an arteriovenous fistula which provides vascular access to a patient on hemodialysis.

7. The adhesive bandage according to claim 1, wherein the sterile pad is located in a central zone of the support.

8. The adhesive bandage according to claim 1, wherein the adhesive bandage is packaged within in a sterile wrapping.

9. An adhesive bandage for application to an epidermis area which is sensitive to contamination by bacterial germs, the adhesive bandage comprising:

a support having an adhesive side with a sterile pad situated on the adhesive side of the support, a protective film covering and the sterile pad and the adhesive side, the protective film having first and second detachable tabs, the first detachable tab comprising a first flap and a second flap separated from one another by a folding line, the first flap being applied to the adhesive side of the support and extending from a first extremity of the support toward a second extremity of the support so as to cover at least the adhesive side adjacent the first extremity and entirely cover the sterile pad with the folding line of the first detachable tab being between the sterile pad and the second extremity, and the second flap extends from the fold line, in a direction toward the first extremity of the support, so as to fold back over the first flap; and the second detachable tab comprising a third flap covering at least the adhesive side adjacent the second extremity, and a remote end of the second detachable tab extending toward the first extremity;

wherein the second flap (18) extends, in the direction of the first extremity of the support (11), over the first flap (17) at least beyond the area of the sterile pad (13) so as to cover completely the sterile pad (13), the second detachable tab (15) comprises a fourth flap (20), formed integral with the third flap (19), which extends, commencing at the folding line (16), in the direction of the first extremity of the support (11) over the first detachable tab (14) at least beyond the sterile pad (13) so as to cover completely the sterile pad (13), and the second detachable tab (15) is arranged to be removed from the adhesive side (12) of the support (11) before the first detachable tab (14); the fourth flap (20) has a length greater than a length of the first flap (17) and extends beyond the first extremity of the support (11); and the second flap (18) has a length greater than a length of the first flap (17) and greater than a length of the fourth flap (20), and the second flap (18) extends beyond the first extremity of the support (11) and beyond the fourth flap (20).

10. The adhesive bandage according to claim 9, wherein the acutely affected area of the epidermis is a site for implementation of an arteriovenous fistula which provides vascular access to a patient on hemodialysis.

11. The adhesive bandage according to claim 9, wherein the sterile pad is located in a central zone of the support.

12. The adhesive bandage according to claim 9, wherein the adhesive bandage is packaged within in a sterile wrapping.

* * * * *